United States Patent [19]

McJames et al.

[11] Patent Number: 5,776,268
[45] Date of Patent: Jul. 7, 1998

[54] PROCESS FOR MANUFACTURING SURGICAL NEEDLES

[75] Inventors: William McJames, Belle Mead; Bernard M. Willis, East Brunswick; Daniel Smith, Manalapan Townshiip; Eugene Reynolds, Freehold; Carl Gucker, Branchburg; Michael Nordmeyer, Neshanic Station, all of N.J.

[73] Assignee: Ethicon, Inc., Somerville, N.J.

[21] Appl. No.: 882,064

[22] Filed: Jun. 25, 1997

Related U.S. Application Data

[63] Continuation of Ser. No. 773,809, Dec. 19, 1996, abandoned, which is a continuation of Ser. No. 633,607, Apr. 17, 1996, abandoned, which is a continuation of Ser. No. 405,554, Mar. 15, 1995, abandoned, which is a continuation of Ser. No. 147,435, Nov. 1, 1993, abandoned.

[51] Int. Cl.⁶ .................................................. C21D 6/00
[52] U.S. Cl. .......................... 148/656; 148/599; 148/600; 163/1; 163/5; 72/354.2; 72/368
[58] Field of Search ........................ 148/656, 598, 148/599, 600; 163/1, 2, 3, 4, 5; 72/343, 368, 352, 362, 372, 354.2

[56] References Cited

U.S. PATENT DOCUMENTS

| | | |
|---|---|---|
| 1,861,358 | 5/1932 | Potter .................................. 163/5 |
| 2,620,028 | 12/1952 | Kohut . |
| 2,652,577 | 9/1953 | Chiaberta ............................. 10/2 |
| 2,939,505 | 6/1960 | Bucher et al. ...................... 153/1 |
| 3,408,846 | 11/1968 | Schofield ............................ 72/254 |
| 3,986,468 | 10/1976 | Szostak et al. .................... 112/222 |
| 4,455,858 | 6/1984 | Hettich ............................... 72/324 |
| 4,491,167 | 1/1985 | Lange et al. ........................ 163/1 |
| 4,672,734 | 6/1987 | Kawada et al. ................... 29/517 |
| 4,785,868 | 11/1988 | Koenig, Jr. ......................... 163/5 |

FOREIGN PATENT DOCUMENTS

| | | | |
|---|---|---|---|
| 27 37 648 | 3/1979 | Germany | B21G 1/02 |
| 2737648 | 3/1979 | Germany | 163/1 |
| 34 14 262A1 | 10/1985 | Germany | B21G 1/04 |
| 62-110828 | 5/1987 | Japan | B21G 1/02 |
| 1-162532A | 6/1989 | Japan | B21G 1/08 |
| 1-166838A | 6/1989 | Japan | B21G 1/02 |
| 222648 | 10/1924 | United Kingdom . | |

*Primary Examiner*—Sikyin Ip
*Attorney, Agent, or Firm*—Emil Richard Skula

[57] ABSTRACT

A process for progressively manufacturing cutting edge needles or wire members. Needle blanks or wire blanks are cut from a roll of wire and mounted to a carrier strip. The carrier strip and needles are moved through a succession of coining dies and at least one trimming die, wherein the first coining die is an open coining die and the one or more successive coining dies are closed coining dies. The needle blanks or wire members are optionally curved, heat treated and electrochemically treated resulting in cutting edge needles or wire members formed without a grinding step and without adversely affecting point ductility.

4 Claims, 16 Drawing Sheets

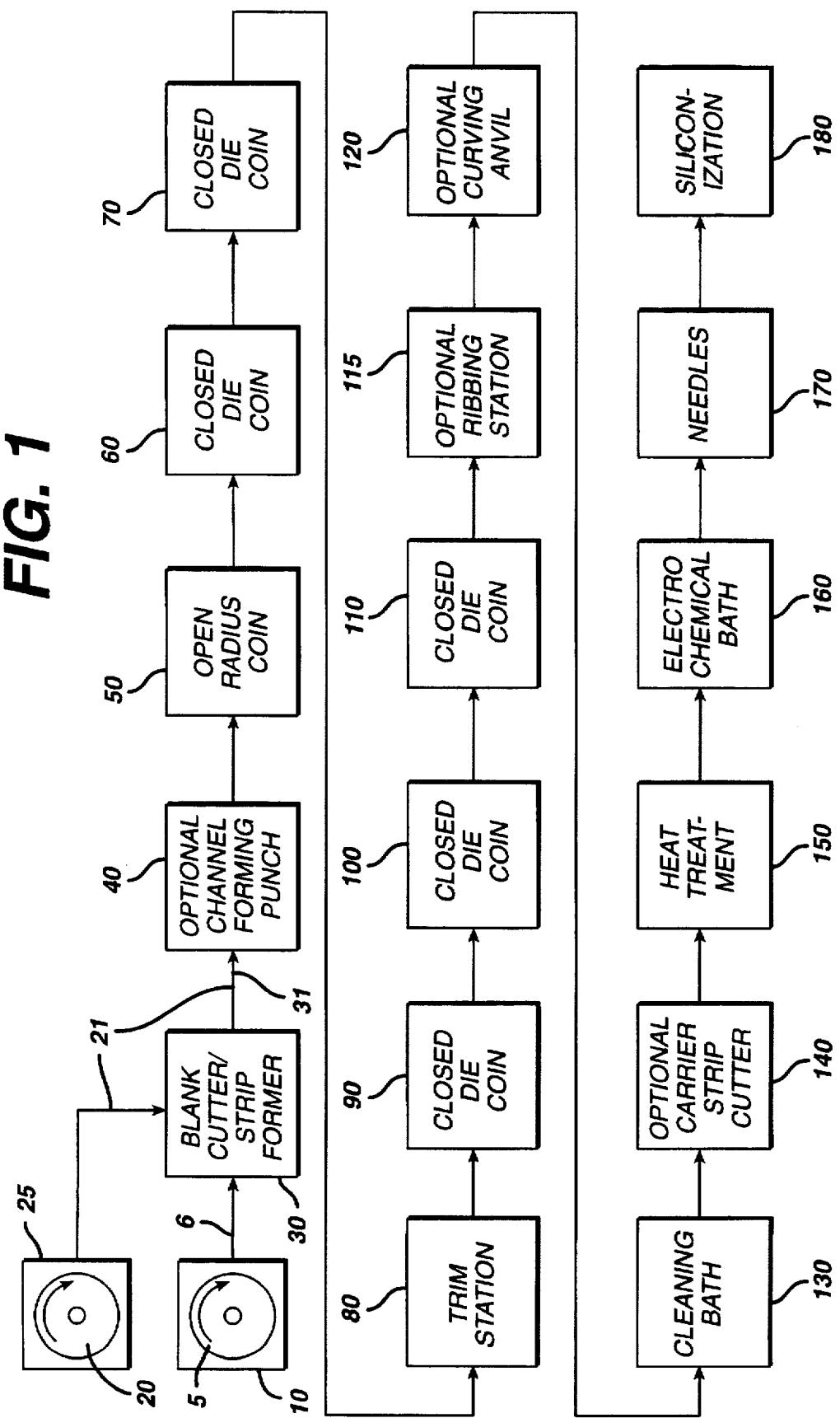

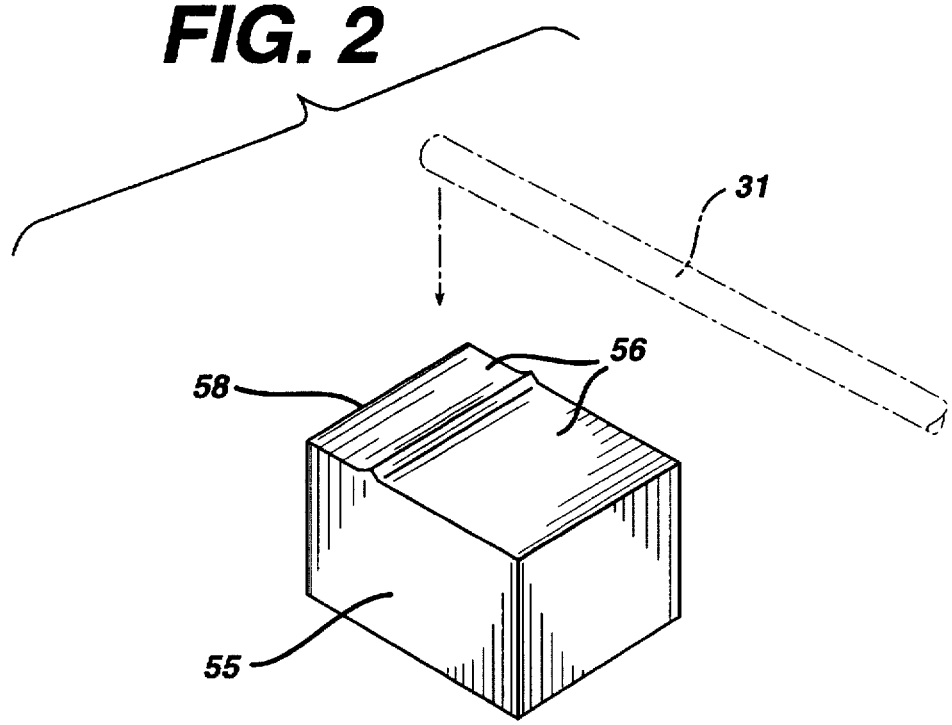
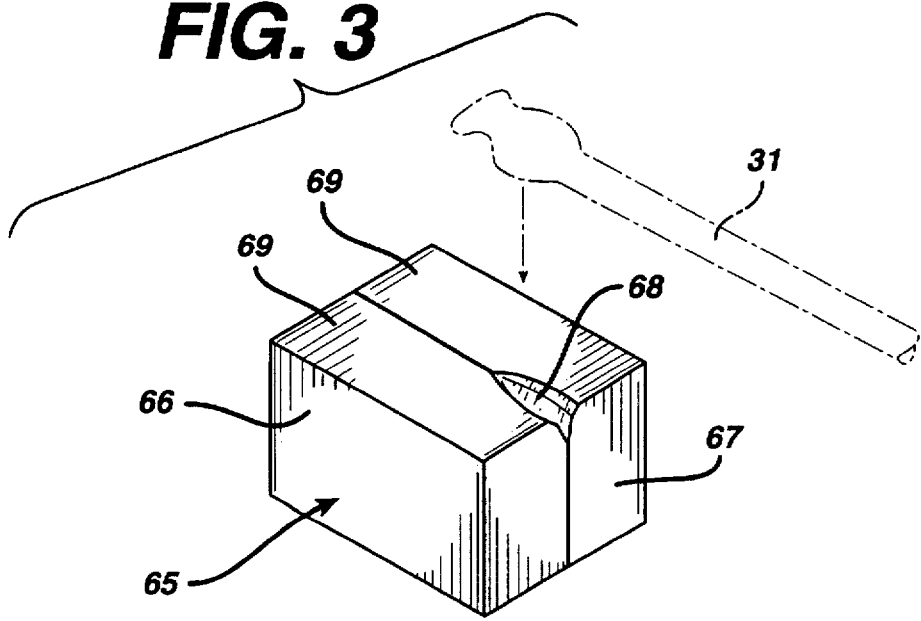

PROCESS FOR MANUFACTURING SURGICAL NEEDLES

This is a continuation, of application Ser. No. 08/773,809, filed Dec. 18, 1996, now abandoned. This is a continuation, of application Ser. No. 08/633,607 Apr. 17, 1996, now abandoned which is a continuation, of application Ser. No. 08/405,554, Mar. 15, 1995, now abandoned which is a continuation, of application Ser. No. 08/149,435 filed Nov. 1, 1993, now abandoned.

TECHNICAL FIELD

The field to which this invention pertains is surgical needles, more specifically, a method of manufacturing cutting edge surgical needles.

BACKGROUND OF THE INVENTION

Surgical needles and methods of manufacturing surgical needles are well known in the art. Surgical needles typically consist of a shaft-like member, which may be curved or straight. The member has a distal piercing point and a proximal end for mounting or receiving a suture. Surgical needles are typically classified as either taper point needles, wherein the diameter of the shaft tapers to a piercing point, or cutting edge needles wherein the needles have various cutting edges along with piercing points to assist in penetrating various types of tissue. Surgical sutures may be attached or mounted to the proximal ends of surgical needles in various ways. One common way is to have a channel formed into the proximal end of the needle. The channel end typically is die-formed into a needle during the manufacturing process and consists of a U-shaped cavity. When a surgical suture end or tip is placed into the cavity, the channel end is hit with a die one or more times under pressure forcing the sidewalls to close tightly about the suture tip to prevent the suture from separating from the needle. The process of mounting a suture tip to the proximal end of a needle is known in the art as swaging. Another manner in which a suture may be mounted to a surgical needle is by drilling a hole, commonly referred to in the art as a blind hole, into the proximal end of the needle. This can be done using conventional mechanical drilling apparatuses or conventional laser drilling apparatuses. The end or tip of a suture is then inserted into the drilled hole and the section of the proximal end of the needle surrounding the blind hole is swaged in a conventional manner by compressing the end one or more times with various conventional dies. It is also known to mount sutures to surgical needles using conventional adhesives.

Surgical needles are conventionally manufactured from surgical grade alloys such as surgical grade stainless steel, which are purchased from manufacturers in the form of rod or finished wire. The rod is typically drawn into finished wire and rolled onto a spool. The initial step in the manufacture of surgical needles is to remove the wire from the spool, degrease or clean if required, and then cut the wire into sections known as needle blanks. The needle blanks are the precursors of the finished surgical needles. Conventional needle blanks will have a length greater than the length of the finished needle since varying amounts of material will be removed from the blank during the needle manufacturing process.

A conventional process for manufacturing a taper point needle typically consists of taking a needle blank and subjecting the blank to a series of grinding operations. This is conventionally done in the following manner. The needle blanks are fed into a conventional belt/stone grinding machine where they are given a preliminary and/or final tip. The needles are then transported individually or in bulk to a conventional needle drilling station wherein the needles are drilled using conventional carbide or tool steel drill bits to provide a proximal suture mounting cavity. The needles are then typically degreased and moved in bulk to a conventional belt grinding machine for the finish taper grind and a curving machine to produce a conventional curved configuration. The needles are then cleaned, heat treated and may be electrochemically treated to additionally finish the needles. This conventional process is a batch process requiring the handling of the needles in bulk containers to transport them to the various work stations. Needles may become damaged, points dulled, etc., during such bulk transfers. In addition, the needles must typically be individually mounted in chucks in each machine at each work station. Although this chuck mounting step may in some instances be automated, it is typically a time consuming, labor intensive operation.

A conventional method of manufacturing cutting edge needles is described below. Wire is cut into blanks and mounted into chucks as previously described. The distal tips of the needle blank s are then rotary swaged in a rotary swage punch and die to produce a conical point and spud. The spud is next partially cut and the needle blank is moved to a belt/stone grinding machine wherein the tip of the needle blank is given a final grind to create the necessary shape for bayonet closed die forming. The needle blanks are then moved to a bayonet die station where each needle blank and/or tip is die formed into a triangular shape. The needle blanks are then subjected to a series of grinding operations in a conventional belt/stone grinder, for example eight or more, to produce the desired cutting edge configuration. The needle blanks must be moved along the machine by a mechanical transfer device which remounts the needle blanks in chucks after and prior to each grinding step. If such a mechanical transfer device is not available, the chuck mounting is done manually. The needle blanks are typically mounted in chucks during all operations. The extensive movement and handling required by this process may result in damage to the needles, dulling of the points, and associated material transfer problems. In addition, the needle machines used in the prior art process are operator dependent. Each operator tends to set up a machine differently resulting in variability in needle geometry and performance characteristics. Since surgical needles are quality control tested prior to release, the problems associated with the prior art process tend to result in a financial burden upon the manufacturer in that a significant amount of the needles produced may have to be rejected and destroyed.

The previously described processes are antiquated, may be labor intensive if a transfer mechanism is not used and typically utilize low speed, low output equipment. The needles are typically manually handled and transferred between various work stations or machines. Needles are typically transferred between work stations in bulk containers. Each needle must be mounted in a chuck at each work station prior to grinding or coining at that work station and then must be removed after the processing in that work station had been completed. In addition, numerous grinding steps are usually required. Often, needles are damaged, including the dulling of needle points, due to the extensive handling and numerous grinding steps which are present in these processes. Furthermore, the conventional processes are imprecise because of the number and types of grinding steps which must be utilized to produce a needle. This imprecision resultingly yields a significant degree of geometric variability.

Accordingly, what is needed in this art is a process for manufacturing cutting edge needles which is efficient and substantially eliminates manual handling and which does not require grinding.

DISCLOSURE OF THE INVENTION

Therefore, it is an object of the present invention to provide a novel process for manufacturing cutting edge surgical needles.

It is a further object of the present invention to provide a process for the manufacture of cutting edge surgical needles in which dimensions of the finished needles can be precisely controlled, monitored and controlled for long machine runs.

It is yet a further object of the present invention to provide a method of manufacturing cutting edge needles while eliminating grinding, and, to manufacture unique cutting edge needle configurations which cannot be made using conventional grinding processes.

It is still yet a further object of the present invention to provide a process for manufacturing cutting edge needles having improved efficiency.

It is a yet further object of the present invention to provide a cutting edge needle manufacturing process which can be automated as a substantially continuous process, eliminating or minimizing the need for batch processing.

Accordingly, a process for manufacturing cutting edge surgical needles by progressively forming a needle blank is disclosed. The process of the present invention consists of the initial step of cutting needle blanks from a roll of wire and mounting the blanks in a carrier. The carrier will preferably consist of a band having pilot holes for indexing throughout work stations and also having members formed therein for engaging and retaining needle blanks. The carrier transports the blanks through a succession of die forming work stations. The first die station is an open die forming station. Each blank is shaped in the first open die station such that the material gradually is allowed to flow along the surface of the open die. Then each needle blank is moved to at least one additional closed die and die-formed at each station. The needle is then moved to at least one punch and cutting die trim station where manufacturing flash is trimmed from the needle. Optionally, the needle is then transported to at least one additional closed die forming station and one optional additional trimming station. The needle is optionally cleaned, heat treated and finished in an electrochemical bath. The finished needle is optionally siliconized.

Yet another aspect of the present invention is a method of manufacturing cutting edge needles or wire members wherein needle blanks or wire blanks are coined in an open radius die and then subsequently coined in a closed die. The blanks are optionally trimmed and optionally heat treated, curved and electrochemically treated.

Other features and advantages of the invention will become more apparent from the following description and accompanying drawings.

BRIEF DESCRIPTION OF THE DRAWINGS

FIG. 1 is a flow diagram of the process of the present invention which utilizes an initial open radius coining step.

FIG. 2 is a perspective view of an open radius die used in the process of the present invention. A needle blank is shown in phantom as it would appear prior to coining in the open radius die.

FIG. 3 is a perspective view of a closed radius die having a bayonet-type cavity. A needle blank is shown in phantom lines wherein the needle blank has a configuration as it would be seen immediately after being coined in the open radius die of FIG. 2.

BEST MODE FOR CARRYING OUT THE INVENTION

Figure 4A:
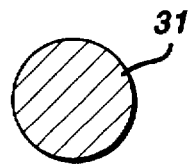
FIG. 4A is a cross-sectional view of a needle blank of the present invention prior to coining.
Figure 16:
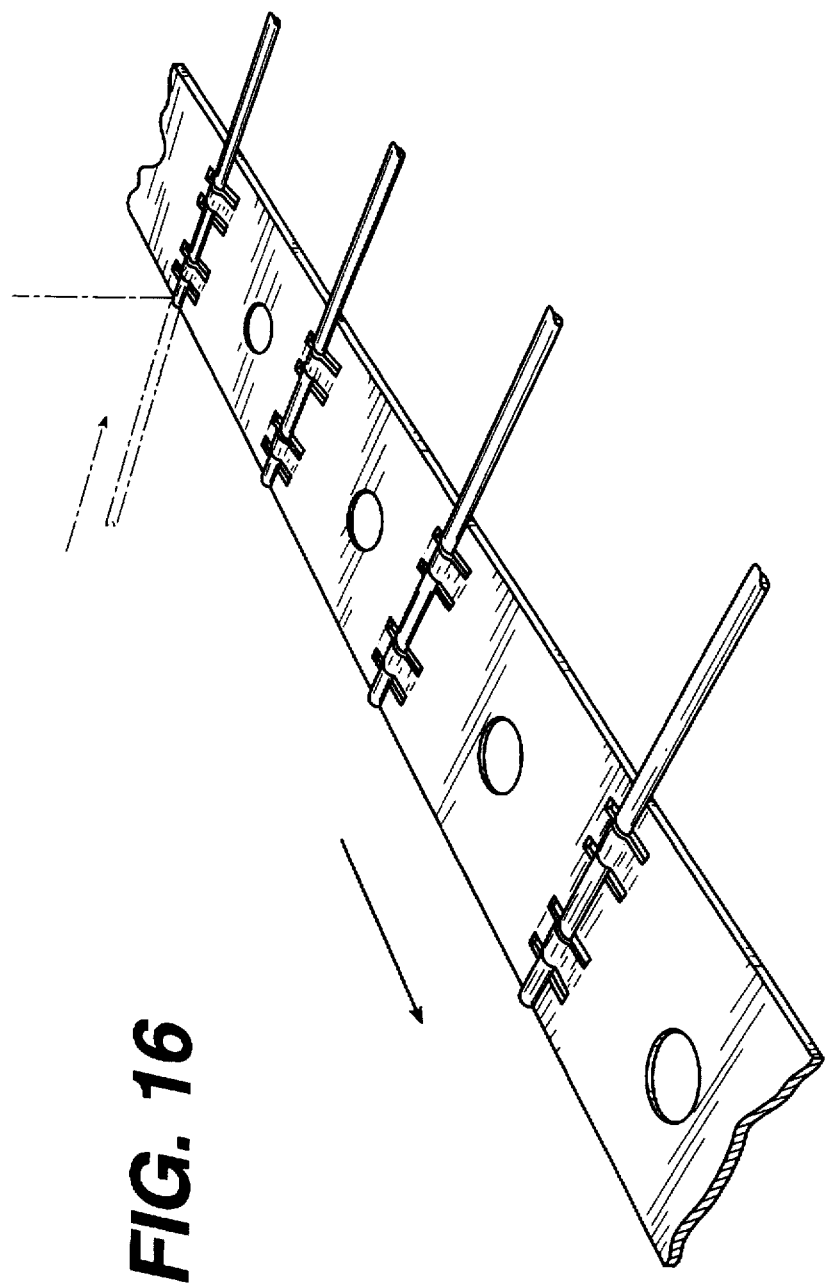
FIG. 16 is a perspective view of a carrier strip containing needle blanks useful in the processes of FIGS. 1 and 7.

Referring to FIG. 1, the flow diagram for the needle manufacturing process of the present invention is illustrated. Initially, wire 6 from a roll 5 is fed by a conventional high speed gripper/feeder machine 10 to blank cutter/carrier strip former machine 30. The roll 5 is rotatably mounted in gripper/feeder 10. Simultaneously, the carrier strip 21 is fed from carrier strip roll 20 to blank cutter/carriage strip former machine 30. The carrier strip roll 20 is rotatably mounted in conventional gripper/feeder machine 25. The carrier strip 21 typically consists of a steel strip known as a bandoleer, the carrier will be sufficiently thick, sufficiently wide and sufficiently flexible to effectively move and retain needle blanks while being capable of being die punched and formed. Preferably the band is made of a flexible metal such as cold rolled steel and equivalents thereof. However, the band may also be made from polymeric materials such as engineered, reinforced polymers and equivalents thereof. The wire 6 being fed from gripper/feeder 10 is cut into lengths which are conventionally referred to as needle blanks 31 within blank cutter/carriage strip former machine 30. As the needle blanks 31 are being cut, the blank cutter/carrier strip former 30 is simultaneously processing the carrier strip 21 in the following manner. Carrier strip 21 is processed to receive needle blanks 21 and to engage indexing controls within the various work stations. The carrier strip 21 (see FIG. 16) is die cut, formed and crimped to produce a carrier strip having indexing pilot holes 25 and crimps which form mounting loops 26 for receiving, engaging and holding needle blanks 31. Then, needle blanks 31 are cut and inserted into the mounting loops 26 of carrier 21 by inserting the wire 6 into each loop 26 and then cutting the wire 6 to from a needle blank 31. The loops 26 are then crimped to retain the needle blanks 31. The needle blanks 31 at this time will have a cross-section as seen in FIG. 4A. The blank cutter/carrier strip former machine 30 consists of three stations including strip forming tool station 37, strip preparation tool station 38 and wire cut-off and strip crimping tool station 39.

Next, the carrier strip 21 having needle blanks 31 mounted therein in crimped loops 26 is moved by a conventional gripper/feeder mechanism to the optional channel forming punch station 40. Movement of the carrier strip to the work stations is indexed to precisely align each needle blank 31 within any of the work stations in the following manner. The carrier strip 21 has indexing pilot holes 25 punched into the carrier strip 21 by the blank cutter/strip former 30. The pilot holes mate with pilots mounted at each work station which engage the pilot holes. The pilots consist of a moveable pin which extends into the pilot holes 25. The strip 21 is indexed by a strip feed wherein pilot pins enter, engage and lock the carrier strip 21 into a precisely aligned position within a work station tool. Needle blanks 31 may be mounted at different intervals along the carrier strip 21 for example from 0.5" to 1.0" intervals. Because of the spatial layout of the tooling, not every needle blank 31 is within a work station at a given time. Some needles on carrier strip 21 will be indexed into a particular work station while other needles will be queued up for work stations. If desired, the carrier strip 21 may be a continuous endless carrier which is reused during the needle manufacturing process. The strip would have the pilot holes 25 and tabs 26 and needles would be removed from the endless carrier at a convenient stage of the process, and remounted to one or more additional carrier strips. One skilled in the art will appreciate that the needle blanks 31 may also be mounted to the carrier strip 21 by alternate methods, if desired although not preferred, including welding, clips, adhesives, snap fits, and the like. The bandoleer strip could, if desired, be replaced by a member comprising lattice of two or more wires. As described in more detail below, the blank cutter/carrier strip former station 30 consists of substation 37, strip forming wherein pilot holes 25 and loops 26 are formed, substation 38, strip preparation, and substation 39, wire cut-off and strip crimping wherein the wire is fed into loops 26 and cut-off to form blanks 31 and the blanks 31 are crimped in loops 26.

In the optional channel forming punch station 40, a channel for receiving a suture is formed into the proximal end of the needle blank. A conventional die and punch is used to form the channel in the proximal end of the blank 31. Sufficient pressure is exerted upon the needle blank 31 in the die of channel forming punch 40 to effectively form and control a channel therein. If desired, the channel forming step could be eliminated and the needles could receive conventionally drilled proximal mounting cavities either during or subsequent to the process.

Figure 4B:
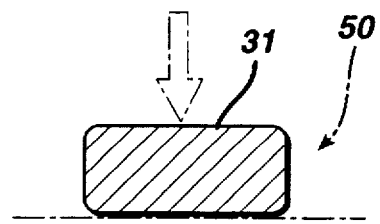
FIG. 4B is a cross-sectional view of a needle blank after it has been coined in the open radius die.

Next, the needle blank 31 having a channel formed in its proximal end is moved with the carrier 21 to the open radius die coin station 50. The open radius coin die station 50 consists of an open radius die 55, preferably as seen in FIG. 2. The term open radius die is defined to mean a die having a open contoured surface without a cavity which allows material to spread over the contour of the die when struck with a punch. An open radius die tends to move material more easily to allow the needle blank 31 to stay more ductile. The open radius die 55 of FIG. 2 is seen to be a flat die which has a curved surface 56 extending from the top surface 56 upward to the distal end 58. As previously mentioned, the needle blank 31 is aligned or indexed precisely within the die 55 of open radius coin die station 50 by the use of the pilot holes 25, which are formed in carrier strip 21 by the blank cutter/carriage strip former machine 30. The distal end of needle blank 31 is coined in the open radius coin die to produce a profile which appears curved from a side view and flattened from a top view. The needle blank 31 is seen in phantom perspective in FIG. 3 after it has been coined in die 55. A cross-sectional view of needle blank 31 after coining in open radius die 55 is illustrated in FIG. 4B. If desired, although not preferred, the needle blank 31 may be moved to an optional trim station prior to the open radius coin die station wherein the distal end of the needle blank is cut or sheared along at least one plane such that the plane is angulated with respect to the longitudinal axis of the needle blank 31.

The terms "coined" and "coining" as used herein are defined to mean forming or reshaping a metal member by applying sufficient pressure to the member to effectively cause the metal to flow into a cavity or onto a surface of a die and to thereby assume, in whole or in part the shape of the cavity or the surface of the die.

The needle blank 31 is then moved by carrier 21 from open radius die coin station 50 to closed die coin station 60.

Figure 4C:
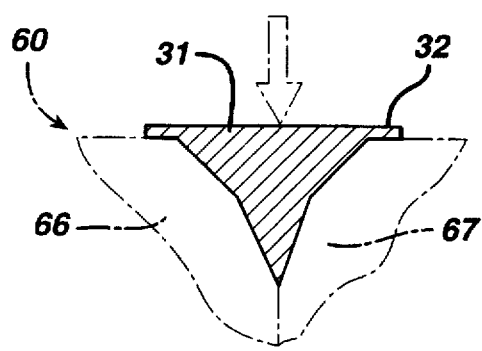
FIG. 4C is a cross-sectional view of the needle blank after it has been coined in the first closed die.
Figure 4D:
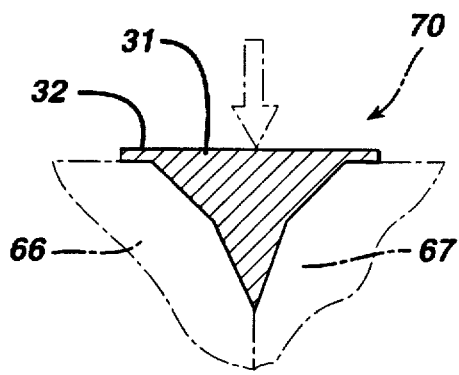
FIG. 4D is a cross-sectional view of the needle blank after it has been coined in the second closed die.

The closed die coin station 60 utilizes a conventional bayonet-shaped closed die 65 to form sides and a point into the needle blank 31. The closed die 65 is illustrated in FIG. 3 and is seen to be a split die having halves 66 and 67, cavity 68 and top surface 69. The needle blank 31 is coined in the closed die 60 using sufficient pressure exerted by a conventional punch to effectively cause the material from the needle blank 31 to flow into the die cavity 68 and substantially assume the configuration of the die cavity 68. The needle blank 31 is coined by striking the needle blank 31 with a conventional punch. The needle blank 31 will have a cross-sectional configuration as illustrated in FIG. 4C. the wing members 32 are seen to extend from both sides of the top of needle blank 31. The needle blank 31 is then moved to a second closed die coin station 70 where it is once again die formed in a die 65. The needle blank 31 will have a cross-sectional configuration as seen in FIG. 4D after being coined in coining station 70.

Figure 4E:
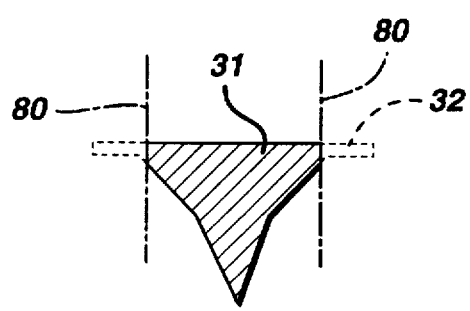
FIG. 4E is a cross-sectional view of the needle blank after it has had wings trimmed off in a punch and cutting die station.
Figure 4F:
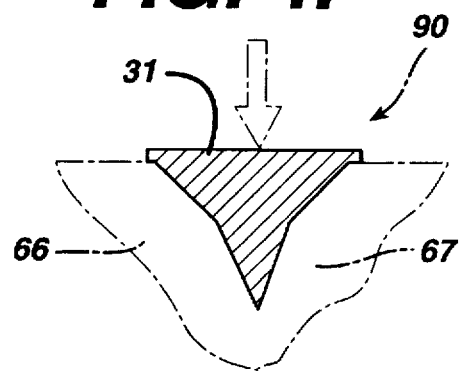
FIGS. 4F–4H illustrate cross-sectional views of the needle blank of FIG. 4E after it has been coined in successive coining stations illustrating the progressive forming.

After exiting the closed die station 70, the needle blank 31 is moved to the trim station 80. In the trim station 80, wing-like projections ("wings") 32 are removed from the needle blank 31 in the following manner. A punch and die with matching shapes precisely cut away the desired amount of excess material from the distal end of the needle blank 31. A cross-sectional view of needle blank 31 after having been trimmed in trim station 80 is seen in FIG. 4E. Wings are often referred to as manufacturing flash. It will be appreciated by those skilled in the art that equivalent trimming methods may be utilized.

The wings are formed in the bayonet cavities 68 of dies 65 of closed die coin stations 60 and 70 as material from the needle blanks 31 is forced to flow into the cavities 68 while material is also forced out of the cavities 68 into the space between the flat top surfaces 69 of the dies 65 surrounding the bayonet cavities 68 and the punch. In the closed dies 65 used in the process of the present invention, a punch forces material from needle blank 31 into the bayonet-shaped cavities 68. The formation of wings is desirable to insure that the cavities 68 are completely filled by blanks 31 and is controlled by controlling the punch height and the volumes of both the bayonet cavities 68 and the wire blank 31.

Figure 4G:
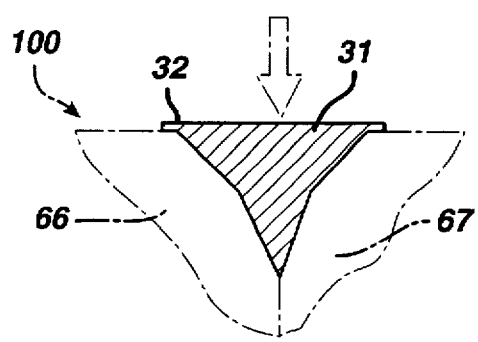
Figure 4H:
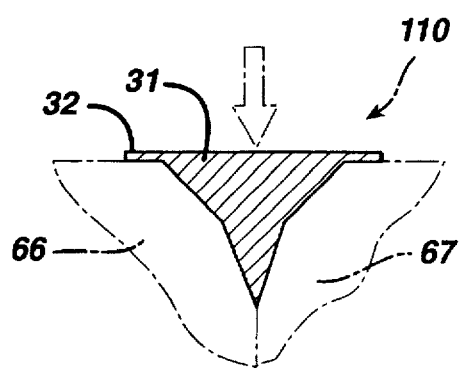
Figure 4I:
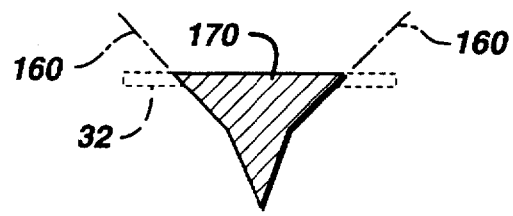
FIG. 4I is a cross-sectional view of the needle blank of FIG. 4H showing in phantom the residual wings, or manufacturing flash, removed by electrochemical treatment. This is a cross-sectional view of a finished needle.

After exiting trim station 80, the needle blank 31 is then moved by carrier 21 to closed die coin station 90 where it is coined in a closed die having a bayonet cavity in a manner similar to that of closed die coin stations 60 and 70. The needle blank 31 will have a cross-sectional configuration as seen in FIG. 4G after being coined in coining station 90. The needle blank 31 is then moved successively to closed die coin station 100 and closed die coin station 110. The needle blank 31 will have a cross-sectional configurations seen in FIG.4H after being coined in coining station 100, and, the blank 31 will have a cross-sectional configuration as seen in FIG. 4I after being coined in station 110. After the needle blank 31 has been coined in closed die coin station 110, it substantially has the cross-sectional configuration of a cutting edge needle with the exception of residual wing members 32 extending from either side of the top of the needle blank 31. If desired, although not preferred, the top of the needle blank 31 may be processed using conventional apparatuses, e.g., grinding, to reduce the thickness of the wings 32 prior to electrochemical treatment. The wing members 32 are subsequently removed from the blanks 31 in the electrochemical bath 160 as further described hereinbelow. In addition, after exiting station 110, the needles are optionally given conventional top and bottom flats in conventional ribbing station 115.

Figure 5:
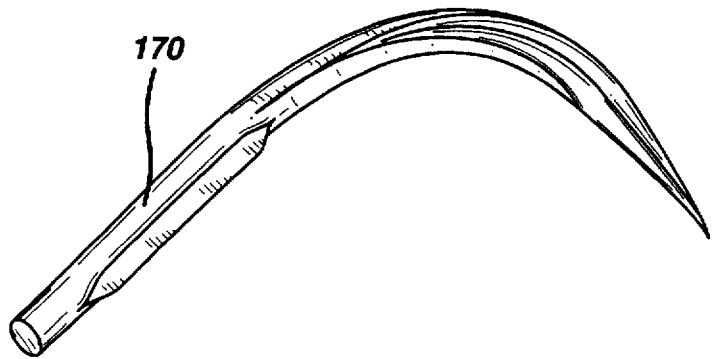
FIG. 5 is a perspective view of a cutting edge needle manufactured by the process of the present invention.

The carrier strip 21 and needle blank 31 (having wings 32) are then moved to the multiple curving anvils machine station 120 where the needle blank 31 is given as required a conventional curved configuration typical of a surgical needle. Next, the needle blank 31 and carrier strip 21 are moved to a clean and dry bath station 130 to remove any residual oils, dirt, particulates, etc. Then, the carrier strip 21 and the needle blank 31 are moved to the carrier strip cutter apparatus 140 which cuts the carrier strip into sections containing a plurality of needle blanks 31. The sections of carrier strip 21 containing needle blanks 31 may be loaded into a tray to facilitate additional processing. If so desired, the carrier strip 21 containing needle blanks 31 may be rolled onto a spool rather than being cut into strips. Prior to such rolling, the needle blanks are turned 90° (in carrier strip 21) from their coining position. The needle blanks 31 are then heat treated in heat treatment apparatus 150. The needles are heated in a conventional heat treatment or tempering process to a sufficient temperature and held for a sufficient length of time at that temperature to effectively harden the needle blanks 31. Next, the proximal suture mounting ends of needle blanks 31 are optionally annealed in a conventional annealing process using conventional annealing apparatuses and then placed in an electrochemical bath 160 and held in the bath 160 for a sufficient period of time to effectively remove any residual wing members 32 thereby producing finished needles 170. It will be appreciated that the electrochemical treatment may be optional depending upon manufacturing specifications, etc. In addition, it will be appreciated that equivalent wing removal processes may be used. A finished needle 170 is illustrated in FIG. 5. The needles 170 are optionally siliconized in optional siliconizing station 180. siliconizing station 180 consists of a conventional siliconizing process, including immersion or spraying, using conventional siliconizing materials.

If desired, the process of the present invention can be modified by not placing the needle blanks 31 into a carrier 21, but rather using conventional chucks and "walking beam" type movement systems. In addition, The process may alternately be practiced by moving needle blanks 31 directly to an open radius die station such as station 50, then moving the blanks to a closed die station such as station 60 to produce a cutting edge needle. In a variation of the first alternate process, a second alternate process utilizes the open radius and closed die coining steps of the first alternate process and additionally the needle blanks are then processed in a trim station such as station 80 to produce the cutting edge needles.

The open radius coining station 50 operates in the following manner. The punch and open radius die 55 trap and reshape the material of the tip of needle blank 31 between the punch and the curved surface 56 of the open radius die 55. This allows free flowing of the metal and also reduce work hardening of the metal.

The closed die coining stations 60, 70, 90, 100 and 110 operate in the following manner. As the needle blank 31 is moved to each successive coining station, the closed dies 65 and punches at each coining station progressively coin and reshape the tip of the needle blank 31 to approach the desired needle shape having the desired cross-sections as seen in FIGS. 4A–L.

The curving anvil machine 130 used in the process of the present invention is a conventional apparatus which operates in the following manner. A needle blank 31 is held over an anvil while a roller moves up to curve a portion of the needle blank 31. Multiple anvils/rolls may be used. The curving anvil machine 130 consists of one or more anvils having the desired radii. Each anvil is mounted to a support frame.

The cleaning bath 130 operates in the following manner. The strip 21 and needle blanks 31 are placed into a reservoir containing a conventional aqueous cleaning solution such as an aqueous solution of a conventional non-caustic detergent. A conventional ultrasonic transducer is mounted in the reservoir. A conventional ultrasonic generator drives the transducer. The needle blanks 31 and strips 21 are rinsed and dried prior to removal from bath 130 using a clear hot water rinse followed by a high velocity air flow.

The carrier strip cutter 140 operates in the following manner. As the carrier strip 21 is fed into carrier strip cutter 140, a conventional die and punch is used to cut the strip into pre-determined lengths.

The heat treatment apparatus 150 operates in the following manner utilizing the following cycle carrier strips 21 containing needle blanks 21 are placed onto trays. The trays are then loaded into a conventional heat treatment oven. The oven is brought to a sufficiently high temperature for a sufficient length of time to effectively harden the needle blanks 31. The process cycle temperatures and times are conventional in the art for processing metals. As previously mentioned, the carrier strip 21 containing blanks 31 maybe rolled onto a spool rather than being cut into strips. The entire spool would then be heat treated in apparatus 150.

The proximal suture mounting ends of needle blanks 31 are annealed in a conventional manner using conventional annealing apparatus. The electrochemical bath apparatus 160 consists of a conventional anodic electrochemical bath. Residence time of the needle blanks 31 in the bath will be sufficient to effectively remove any residual material which may be present on the needle blank 31 including any residual manufacturing flash such as residual wing members 32. The chemical composition of the bath and voltages are conventional in this art. The electrochemical bath mixture comprises an aqueous, acidic mixture.

The electrochemical bath 160 operates in the following manner. The needle blanks 31 remain the strips of carrier 21 and are placed in the aqueous bath for a sufficient amount of time at a sufficient voltage to effectively remove residual material such as residual metal flash from the needle blanks 31, thereby forming the finished needles 170. If desired, the needles 170 may also be give a conventional siliconizing treatment using known and accepted silicone compounds applied using known application methods.

Figure 6:
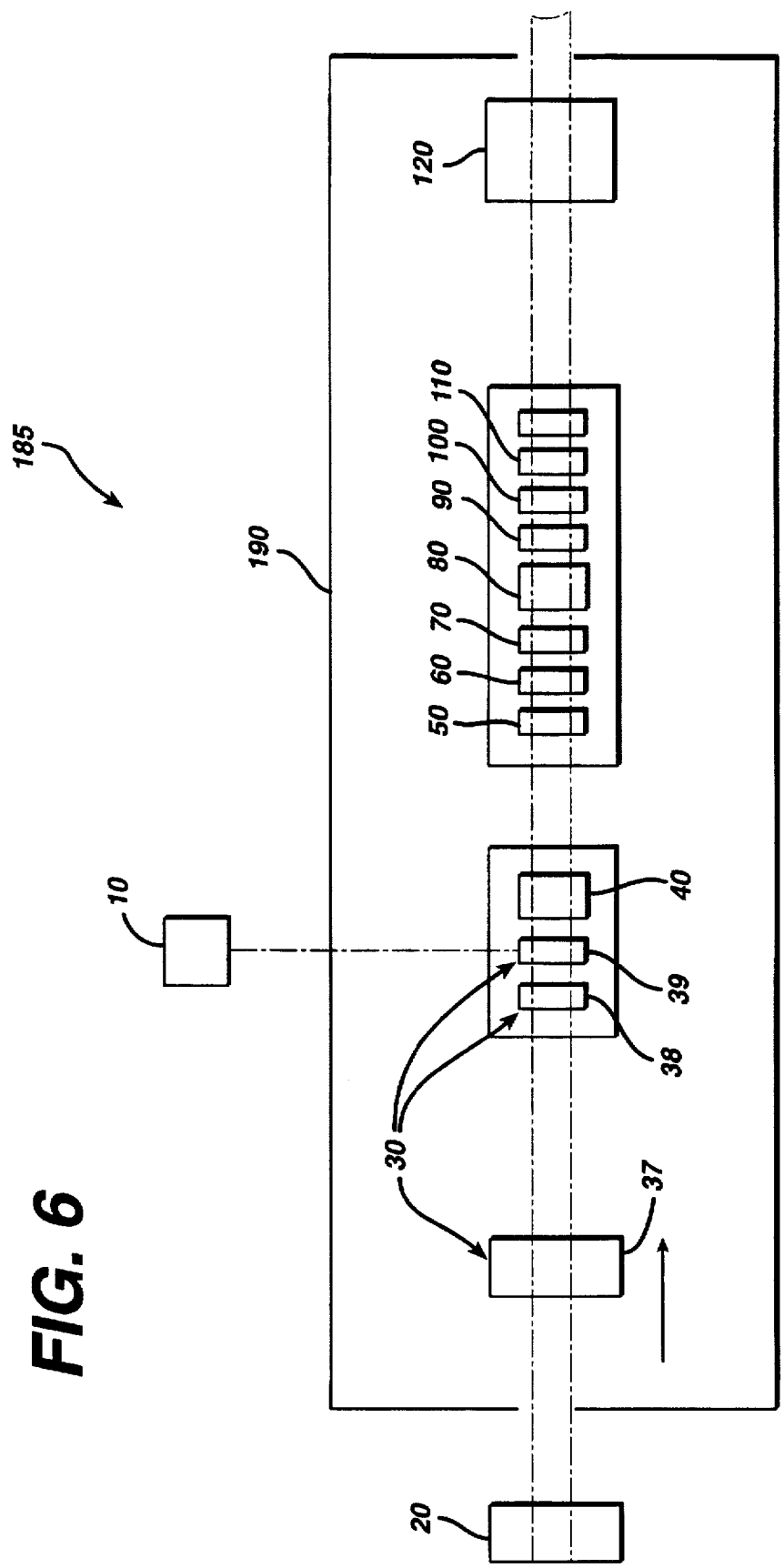
FIG. 6 is a schematic view of the layout of the machinery utilized to manufacture needles in the process of the present invention.

The coining stations and trimming stations utilized in the process of the present invention will consist of punches and dies mounted to frames which are in turn preferably mounted to a unitary forming machine 180(see FIG. 6). It will be appreciated that in an automated process of the type described, a needle blank 31 will be successively be moved through the various coining stations and trim stations. At any given time as the needle blank 31 enters a particular station there will be a needle blank entering a subsequent or previous station. All of the stations are operating on different needle blanks 31 at substantially the same point in time so that, for example, as the needle blank 31 is moved to the channel forming punch 40 from the blank cutter/carriage strip former 30, a needle blank 31 is being moved to the curving anvil 120 from closed die station 110. The cleaning bath 130, the carrier strip cutter 140, the heat treatment apparatus 150 and the electrochemical bath 160 are typically not mounted to the forming machine 180. A schematic of the lay-out of the forming machine 180 is seen in FIG. 6. The forming machine consists of a central frame or base 190. Mounted to the base are the various work stations which consist primarily of punches and dies. The punches and dies are powered in a conventional manner. For example, the work stations may be powered by a motor which powers a flywheel having a clutch which in turn transmits power to the work stations with shafts and bullgears. The blank cutter/strip former station 30 is seen to consist of three individual stations including strip forming tool station 37, strip preparation tool station 38 and wire cut-off and strip crimping tool station 39.

Figure 8:
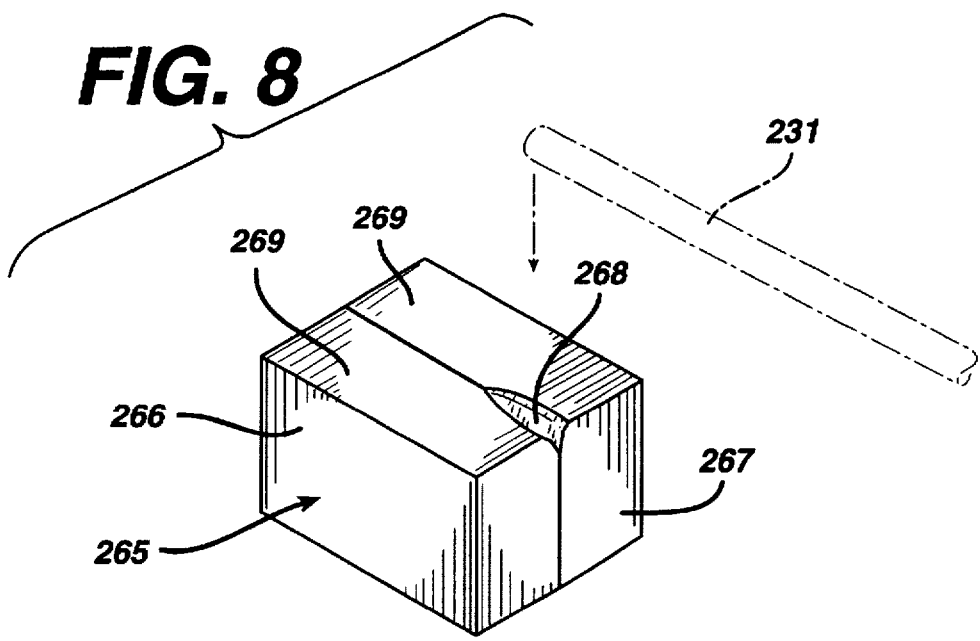
FIG. 8 is a perspective view of a closed die having a bayonet cavity which is used in the process of FIG. 7. A needle blank is shown in phantom prior to the initial coining step.
Figure 9A:
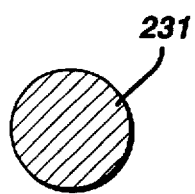
FIG. 9A is a perspective view of a needle blank prior to the initial closed die coining step in the process of FIG. 7.
Figure 9B:
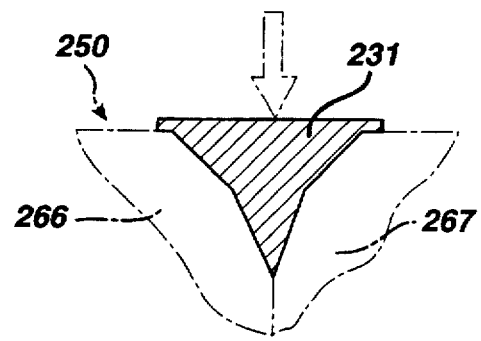
FIGS. 9B–9D illustrate cross-sectional views of the needle blank in successive closed die coining stations illustrating the progressive forming.
Figure 9C:
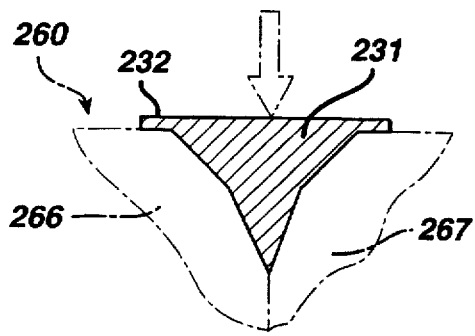
Figure 9D:
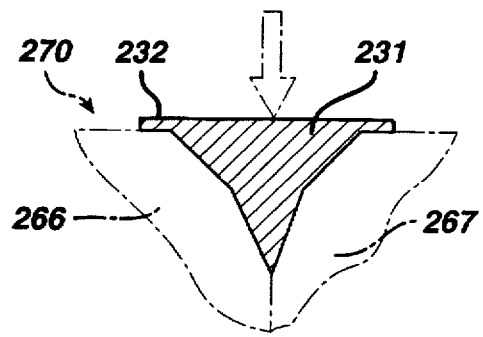
Figure 9E:
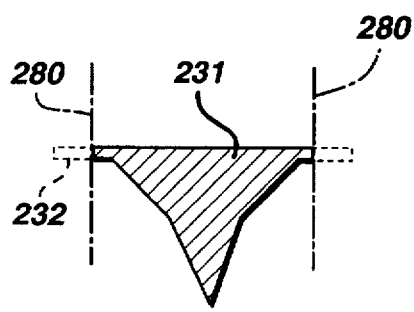
FIG. 9E illustrates the needles blank of FIG. 9D after the wings have been trimmed of f in the punch and die cut trimming station.
Figure 11:
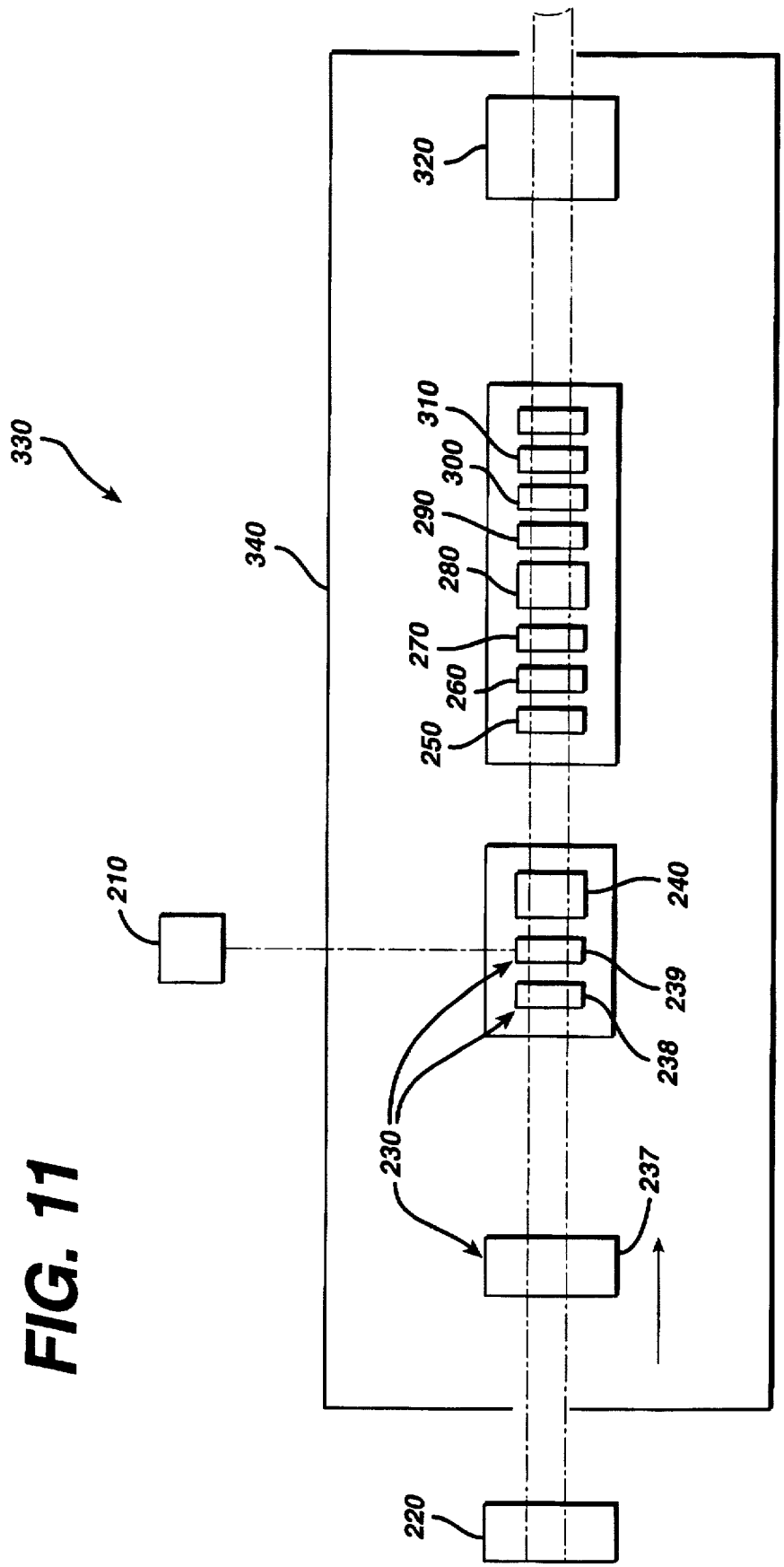
FIG. 11 is a schematic of an equipment layout which can be utilized to manufacture needles in the process of FIG. 7.

A closed die process for manufacturing cutting edge needles is seen in FIG. 11. In that process a wire roll 205 is mounted in conventional gripper feeder 10. Wire 206 is fed to blank cutter/carriage strip former apparatus 30. A carrier strip roll 220 is mounted in gripper/feeder apparatus 225. Carrier strip 221 is fed simultaneously to blank cutter/carrier strip former 230. Wire 206 is cut into blanks 231 in blank cutter 230. Additionally, carrier strip 221 is simultaneously processed by punching and forming to produce pilot holes 225 and loops 226 for retaining the needle blanks 231. The needle blanks 231 mounted in carrier strip 221 will have a substantially circular cross-section prior to coining as seen in FIG. 9A. The blank cutter/strip former station 230 is seen, as further described below, to consist of three individual stations including strip forming tool station 237, strip preparation tool station 238 and wire cut-off and strip crimping tool station 239.Needle blanks 231 are mounted in the loops 226 of carrier strip 221 by crimping and the carrier strip 221 and needle blanks 231 are moved to an optional channel forming station 240 where a channel is die-formed into the proximal end of needle blank 231. As mentioned previously, different configurations for the carrier strip may be used including wires or a continuous endless belt. Then, each needle blank 231 having a channel formed in its proximal end is moved to the first closed die coin station 250 where it is coined and begins to have a cross-section which is somewhat triangular as seen in FIG. 9B. Referring to FIG. 8, closed die 265 is illustrated. Also seen in phantom is needle blank 321 prior to the first coining operation in coining station 250. Then the needle blank 231 and carrier 221 are moved successively to closed die coin stations 260 and 270 to produce, respectively, the cross-sectional configurations as seen in FIGS. 9C and 9D. As mentioned previously, the use of closed die coining to form a needle having a substantially triangular shape produces wings (or wing members) 232 adjacent to either side of the top of the needle blank 231 resulting from material being forced to both flow out of and into the cavities of the closed bayonet-shaped dies 265. These wings 232 must be removed from needle blank 232 during the needle forming process. In the next step of the process, the needle blank 231 and carrier 221 are moved to trim station 280. The previously-mentioned wings 232 are trimmed from each needle blank 231 in the trim station 280 using a punch and cutting die. After being trimmed in trim station 280, needle blank 231 will have a cross-section as seen in FIG. 9E.

Figure 9F:
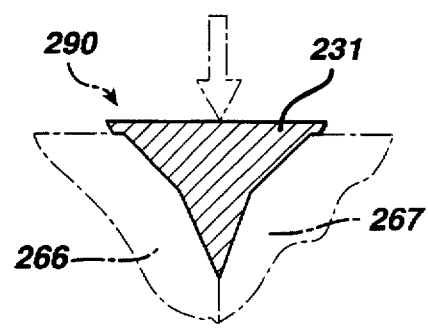
FIGS. 9F–9H are cross-sectional views of the needle blank of FIG. 9E in successive coining stations illustrating the progressive forming of the needle blank.
Figure 9G:
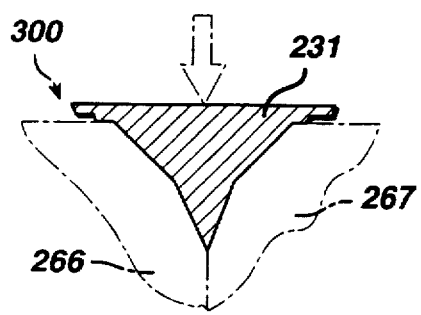
Figure 9H:
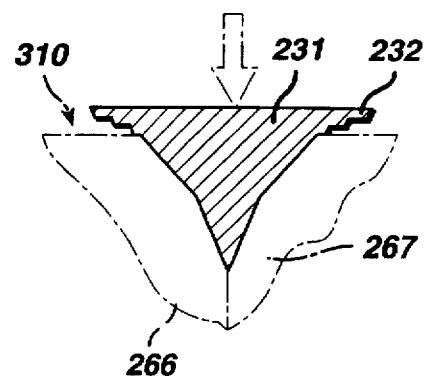
Figure 9I:
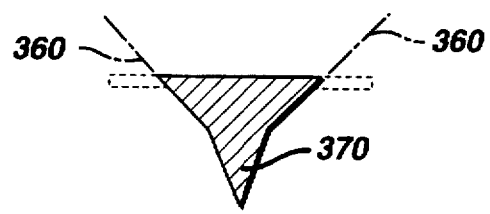
FIG. 9I is a cross-sectional view of the needle of FIG. 9H after the residual wing members have been removed.

Next the needle blank 231 and the carrier 221 are moved to closed die coining station 290 where the needle blank 231 is coined and has a resulting cross-section as seen in FIG. 9F. Then, the needle blank 231 and the carrier 221 are moved successively to closed die coin stations 300 and 310 wherein the needle blank 231 is again coined at each station and has, respectively, cross-sections as seen in FIGS. 9G and 9H. After the coining operation in closed die coin station 310 has been completed, the needle blank 231 substantially has the configuration of a cutting edge needle with the exception that the body of the needle blank 231 is not curved and the needle has residual wings 232 extending from either side of the top surface of the needle (see FIG. 9H). The needle blanks 231 are optionally given top and bottom flat sides in conventional ribbing machine 315. The next step in the process involves moving the carrier strip 221 and needle blank 231 to a curving anvil station 320 wherein the needle blank 231 is given a conventional curved surgical needle configuration. Next the needle blank 231 and carrier 221 are moved into cleaning bath 330 for the removal of residual dirt, oil, grease, particulates, etc. From the cleaning bath 330 the carrier strip 221 and the needle blank 231 are moved to carrier strip cutter 340 where sections of carrier strip 221 containing a plurality of processed needle blanks 231 are cut.

Figure 7:
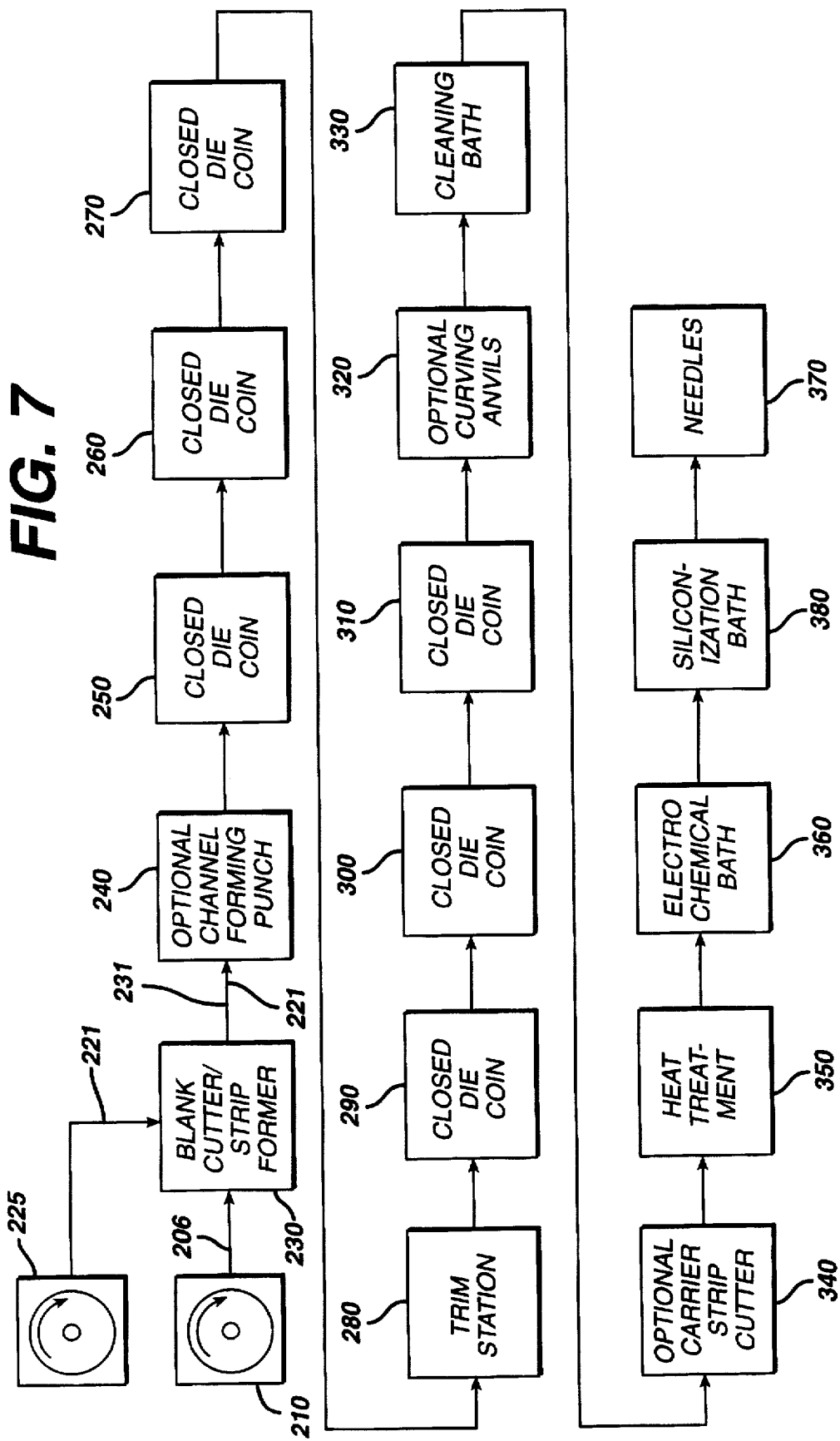
FIG. 7 is a process flow diagram of a process used for manufacturing cutting edge needles without a grinding step which does not utilize an open radius die.
Figure 10:
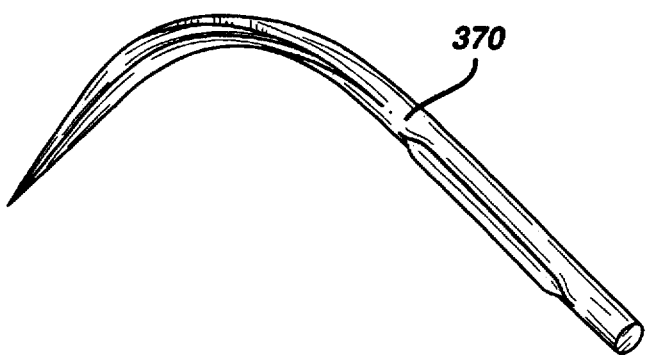
FIG. 10 is a perspective view of a cutting edge needle manufactured by the process of FIG. 7.

Next, the sections of carrier strip 221 containing the needle blanks 231 are placed into a conventional heat treatment apparatus 350 for heat treatment at sufficient temperatures and sufficient times to effectively heat treat the metal. Then, the needle blanks 231 contained in sections of carrier strip 221 are placed into an electrochemical bath 360 and maintained in the electrochemical bath for a sufficient time to effectively remove the wing members 232 from the needle blanks 231 thereby forming needles 370. The equipment use in the process of FIG. 11 is substantially the same as that used for the open die process of the present invention. A perspective view of the finished needle 370 is seen in FIG. 10. If desired, although not preferred, cutting edge needles could be manufactured using the process of FIG. 7 and utilizing a single open radius coin followed by a single closed die coin, and, optionally a single trim station. The needles would then be further processed using any additional processing steps which may be desired.

A schematic of the lay-out of the forming machine 330 is seen in FIG. 11. The forming machine 330 consists of a central frame or base 340. Mounted to the base 340 are the various work stations which consist primarily of punches and dies. The punches and dies are powered in a conventional manner. For example, the work stations may be powered by a motor which powers a flywheel having a clutch which in turn transmits power to the work stations with shafts and bullgears. The blank cutter/strip former station 230 is seen to consist of three individual stations including strip forming tool station 237, strip preparation tool station 238 and wire cut-off and strip crimping tool station 239.

The above described processes may also be used to manufacture wire members having ends with taper points. Typically the processes would be identical wherein wire blanks would be cut from a spool of wire and progressively formed as described above. The heat treatment and curving steps could be omitted, depending upon the application. In addition, one grinding step could be omitted depending upon the nature and type of wire stock utilized to make the wire blanks. Such processes could be used to manufacture, for example, semiconductor leads, fasteners, pins, etc., and equivalents thereof.

Figure 12:
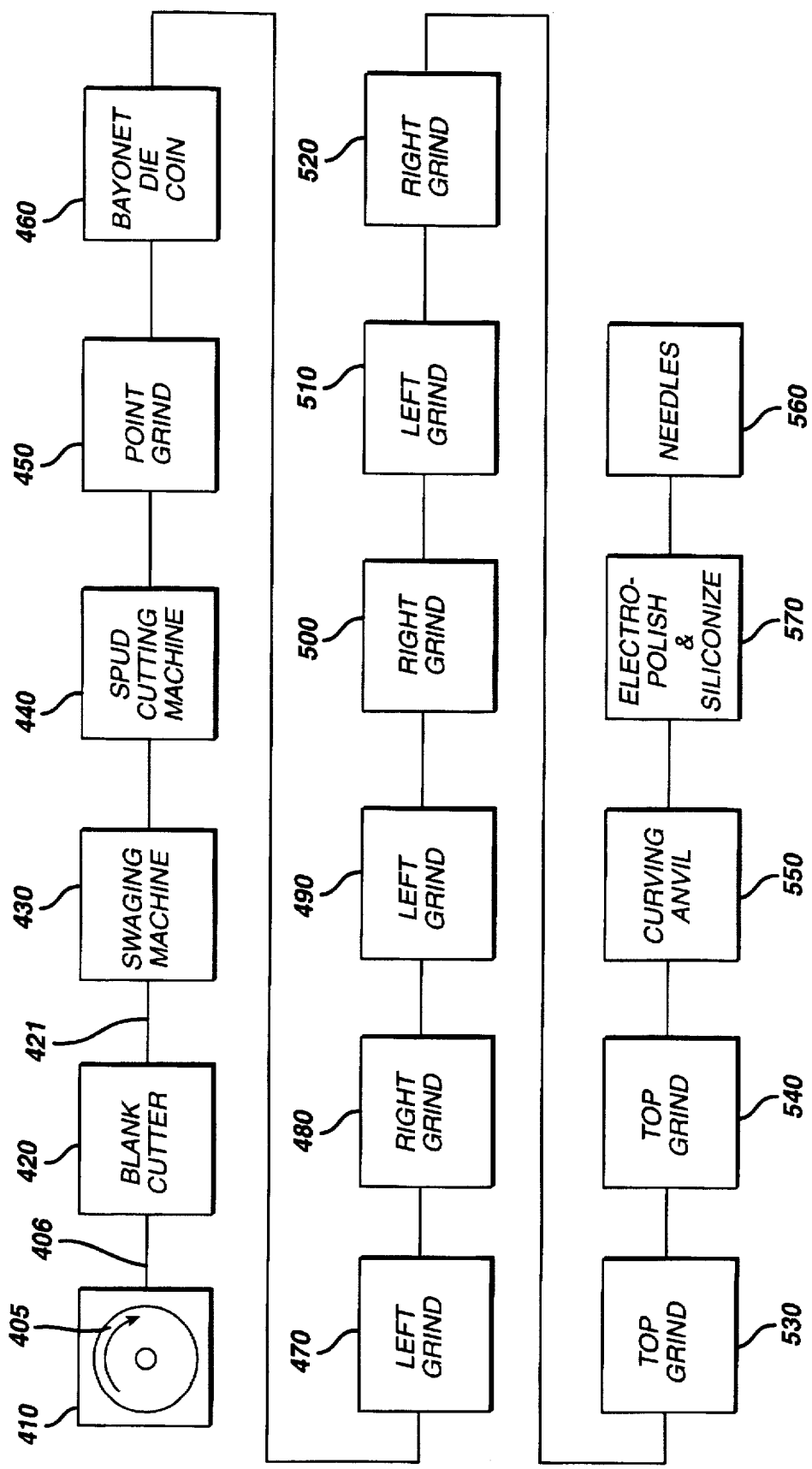
FIG. 12 is a flow diagram of a process of the prior art used to manufacture cutting edge needles containing grinding steps.
Figure 13:
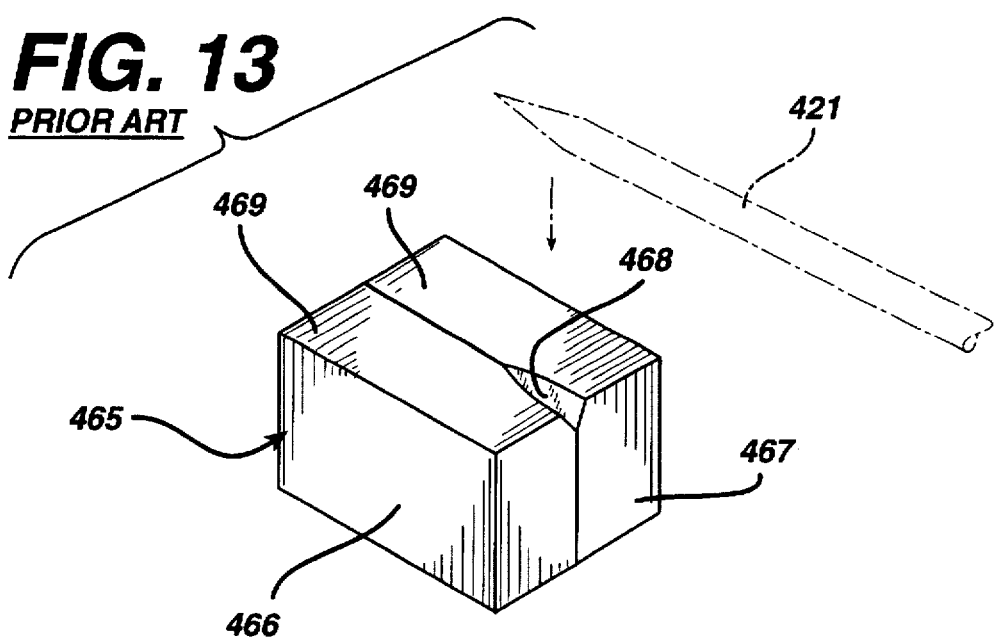
FIG. 13 illustrates a closed die used in the prior art process of FIG. 12.
Figure 15:
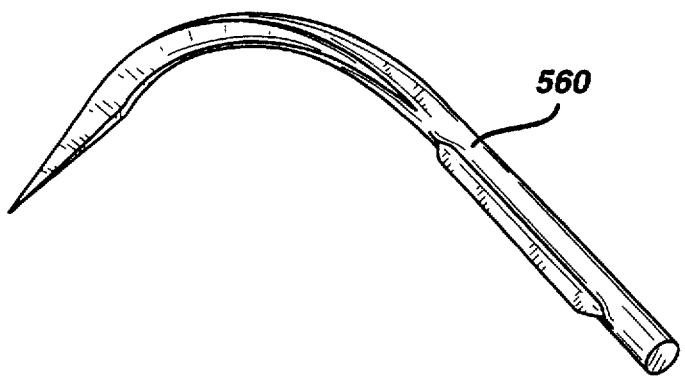
FIG. 15 is a perspective view of a needle produced by the process of FIG. 12.
Figure 14A:
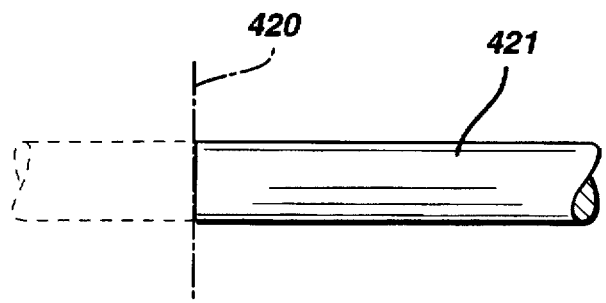
FIG. 14A illustrates a needle blank utilized in the process of the prior art as it is cut from wire.
Figure 14B:
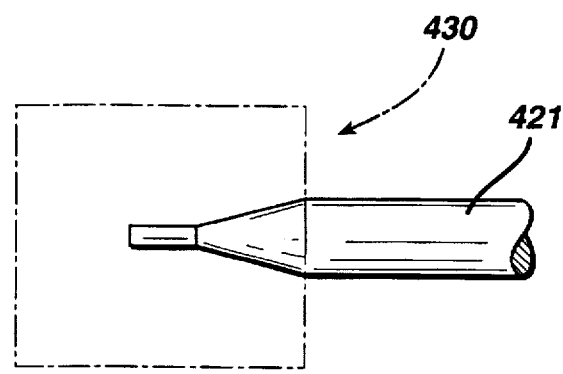
FIG. 14B illustrates the needle blank of FIG. 14A after the distal end has been coined in a rotary swaging die to form a tapered end section having a distal spud.
Figure 14C:
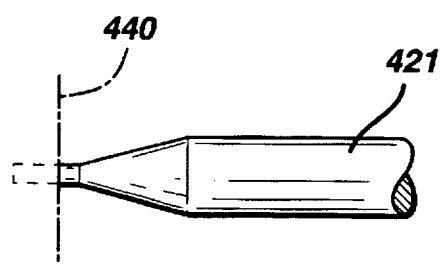
FIG. 14C illustrates the needle blank of FIG. 14B after a section of the distal spud has been trimmed.
Figure 14D:
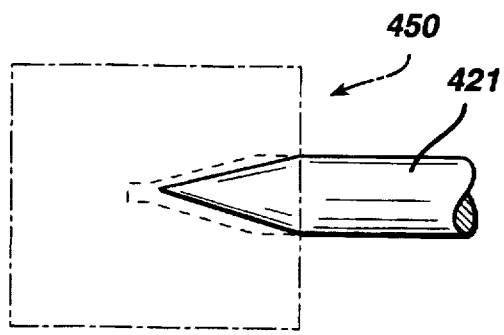
FIG. 14D illustrates the needle blank of FIG. 14C after it has been ground to a tapered point.
Figure 14E:
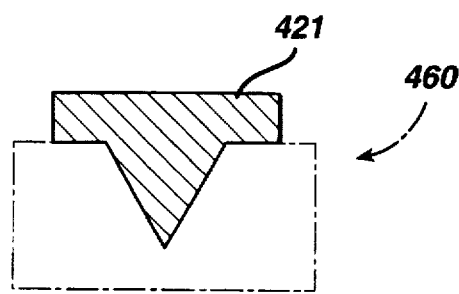
FIG. 14E illustrates the cross-section of the needle blank of FIG. 14D after it has been coined in a closed bayonet die.
Figure 14F:
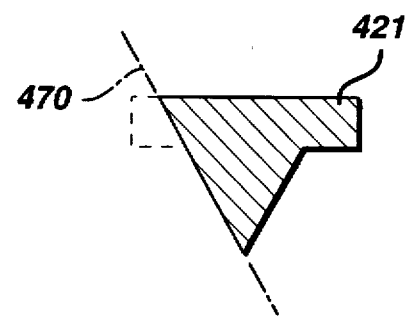
FIGS. 14F–14M illustrate the grinding steps required to produce a conventional cutting edge needle from the needle blank of FIG. 14E.
Figure 14G:
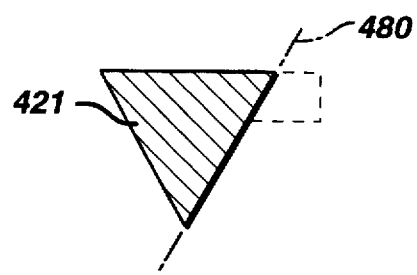
Figure 14H:
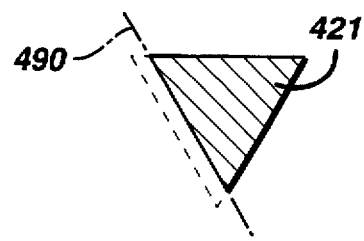
Figure 14I:
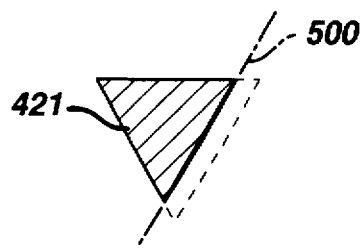
Figure 14J:
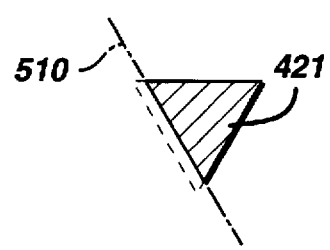
Figure 14K:
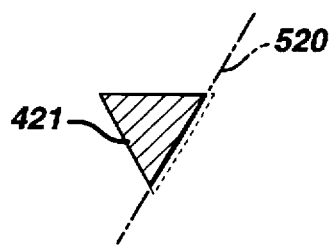
Figure 14L:
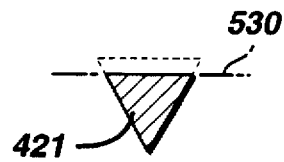
Figure 14M:
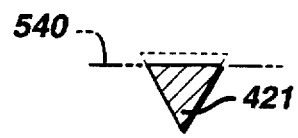

A process of the prior art for making cutting edge needles is illustrated in FIG. 12. In that process, a roll of wire 405 rotatably mounted in a conventional low speed gripper/feeder, is used to feed wire 406 to a conventional blank cutter 420. The needle blanks 421 have a configuration as seen in FIG. 14A. The needle blanks 421 are then processed in a rotary swaging machine 430 wherein a tapered or conical end with a protruding stub 433 is formed into the distal end of needle blank 421 as seen in FIG. 14B. The needle blanks 421 are die-formed or coined in the rotary swaging machine 430, using conventional dies, to have a distal taper portion and a distal spud extending from the taper portion. The needle blanks 421 are then fed into a conventional cutting machine 440 wherein a portion of the spud section 433 of the needle blank 421 is cut away from the distal end section of the needle blank 421 as seen in FIG. 14C. The needle blanks 421 are then passed over a point grinding apparatus 450. The needle blank 421 receives a conventional taper point as a result of the point grinding step as illustrated in FIG. 14D. Then the ground needle blanks 421 are fed into a single conventional coining bayonet die station 460, having closed die 465, wherein the needle blank 421 is coined such that it has a substantially triangular cross-section having wing members 432 extending from the top as seen in FIG. 14E. The coined needle blank 421 is then ground on each side numerous times (typically at least eight times) until the wing members are completely removed and the desired triangular configuration having cutting edges is formed. An eight step grinding process represented by grinding stations 470, 480, 490, 500, 510, 520, 530, and 540 is illustrated in FIG. 12. The grinding process consists of a left grind, a right grind, followed by two successive left and right grinds in turn followed by two top grinds to produce the configuration as seen in FIG. 14M. The configuration of the needle blank 421 after each grinding step is illustrated in FIGS. 14F–14M. The remaining grinding flash is typically polished away in an electrochemical bath. The coined and ground needle blank 421 is then curved in a conventional curving anvil apparatus 480 producing the finished needle 490 as seen in perspective in FIG. 15.

There are numerous disadvantages associated with the process of the prior art. The disadvantages include low manufacturing and process throughput speeds, inconsistency and manufacturing tolerance variation. In addition, the prior art process utilizes loose needles subject to damage and dulling as well as mixing. Another disadvantage is that the process equipment utilized in the prior art process tends to have inherent process variability due to the equipment design. Furthermore, the prior art process requires frequent material transfer in the form of loose needle blanks from machine to machine. These disadvantages are overcome by the processes of the present invention.

The wires or needle wires which can be used in the process of the present invention include conventional needle wires made from metals such as 300 series stainless steel, 400 series stainless steel, or any other wire which can be formed including conventional or known alloys.

The diameter of the needle wire used in the process of the present invention will have a diameter which will depend upon the particular alloy used. For example, the needle wire may have a diameter ranging from 0.001 inches to about 0.100 inches. More typically, wires having a diameter of about 0.010 inches to about 0.080 inches may be used, preferably about 0.015 inches to about 0.080 inches. However other diameters may be used. The length of the needle blank 31 will vary in accordance with the type of needle which is being manufactured. The length of the needle blanks will vary in accordance with several parameters including the wire diameter, desired finished length and the type of needle.

Sufficient force is exerted upon the dies by the punches to effectively coin the wire blanks at each coining station. The forces will depend on the wire material, wire diameter, tool configuration, die configuration, etc. Typically the forces will range from up to about 30 tons or more. However, it will be appreciated that the forces may vary higher or lower depending upon the configuration of the dies and the diameter and material of the needle blank 31.

The use of an initial open die coining step in the process of the present invention, surprisingly and unexpectedly, results in needles having improved tip ductility and allows for the controlled movement of large volumes of metal. It is believed that one explanation for this improvement, although not wishing to be held to any particular theory, may be that since the wire is not trapped in a closed die cavity, less pressure or work is exerted onto the wire, thus allowing the thickness of the wire to be substantially reduced with less trauma known as work hardening. A closed die traps the wire and as the punch is getting closer to the die surface large amounts of material are squeezed out of the die cavity and into an increasingly smaller space between the face of the die and the face of the punch. The radius of the open radius die reduces the material thickness as the needle tip is approached. Eventually, this volume becomes infinitely small.

Although this invention has been shown and described with respect to detailed embodiments thereof, it will understood by those skilled in the art that various changes in form and detail thereof may be made without departing from the spirit and scope of the claimed invention.

We claim:

1. A method for manufacturing a cutting edge surgical suture needle, comprising:

providing an open radius die, said open radius die comprising a curved surface terminating in a distal ridge, wherein said curved surface is continuous;

mounting a plurality of needle blanks to a carrier means, said needle blanks comprising metal wire;

moving the carrier means and each needle blank successively to the open radius coining die;

coining each needle blank on the curved surface of the open radius coining die and thereby causing at least part of each needle blank to flow onto the surface of the open radius die such that the flow is unrestrained laterally;

then moving each needle blank successively to at least one coining die having a cavity and coining each needle blank in each said coining die;

moving each needle blank to a trimming station and trimming off any excess flash;

moving each needle blank to at least one additional coining die having a cavity and coining each needle blank in each coining die, thereby forming a surgical suture needle; and, moving each needle to a curving anvil station and curving each surgical needle wherein the metal wire comprises a metal alloy selected from the group consisting of 300 series stainless steel, 400 series stainless steel and equivalent alloys.

2. The process of claim 1 further comprising the step of heat treating each needle blank to relieve stress and hardening.

3. The process of claim 1 further comprising the step of treating each needle in an electrochemical bath.

4. The process of claim 1 further comprising the step of siliconizing each needle blank.

* * * * *